(12) United States Patent
Leenhoven

(10) Patent No.: US 6,390,092 B1
(45) Date of Patent: May 21, 2002

(54) DEVICE AND METHOD FOR USING OSCILLATORY PRESSURE RATIO AS AN INDICATOR FOR LUNG OPENING DURING HIGH FREQUENCY OSCILLATORY VENTILATION

(75) Inventor: Tom Leenhoven, Beverwijk (NL)

(73) Assignee: Sensormedics Corporation, Yorba Linda, CA (US)

(*) Notice: Subject to any disclaimer, the term of this patent is extended or adjusted under 35 U.S.C. 154(b) by 8 days.

(21) Appl. No.: 09/633,550

(22) Filed: Aug. 7, 2000

(51) Int. Cl.$^7$ ............................................. A61M 16/00
(52) U.S. Cl. .............................. 128/204.23; 128/207.14
(58) Field of Search ........................ 600/529, 532–533, 600/538; 128/204.21, 204.23, 204.25, 205.24, 207.14, 207.15

(56) References Cited

U.S. PATENT DOCUMENTS 5,752,921 A * 5/1998 Orr ............................. 600/533

OTHER PUBLICATIONS

Harris, T.R. et al., "Physiologic Principles", in Goldsmith et al., Assisted Ventilation of the Neonate (W.B. Saunders Company, 1996, pp. 21–68).

Chang, H.K., "Mechanisms of Gas Transport During Ventilation by High–Frequency Oscillation", J. Appl. Physiol: Respiratory, Environmental and Exercise Physiology (1984), 56: 553–563.

Boynton, B.R. et al., "Airway Pressure Measurement During High Frequency Oscillatory Ventilation", Critical Care Medicine (1984), 12: 39–43.

Gerstmann, D.R. et al., "Proximal, Tracheal, and Alveolar Pressures During High–Frequency Oscillatory Ventilation in a Normal Rabbit Model", Pediatric Research (1990), 28: 367–373.

Zobel, G. et al., "Proximal and Tracheal Airway Pressures During Different Modes of Mechanical Ventilation: An Animal Model Study", Ped. Pulm. (1994), 18: 239–243.

Gerhardt, T. et al., "Chestwall Compliance in Full–Term and Premature Infants", Acta Ped. Scan. (1980), 69: 359–364.

Vengegas, J.G. et al., "Understanding the Pressure Cost of Ventilation: Why Does High–Frequency Ventilation Work?", Critical Care Medicine.. (1994), 22: S49–S57.

Pfenninger, J. et al., "Pressure–Volume Curves, Static Compliances and Gas Exchange in Hyaline Membrane Disease During Conventional Mechanical and High–Frequency Ventilation", Intensive Care Medicine (1988), 14: 364–372.

Sly, P.D. et al., "Noninvasive Determination of Respiratory Mechanics During Mechanical Ventilation of Neonates: A Review of Current and Future Techniques", Ped. Pulm. (1988), 4: 39–47.

Isabey, D. et al., "Pressure Change and Gas Mixing Inducing by Oscillations in a Closed System", J. Biomech. Eng., (1985), 107: 68–76.

Dorkin, H.L., et al., "Respiratory System Impedance from 4 to 40 Hz in Paralyzed Intubated Infants with Respiratory Disease", J. Clin. Invest. (1983), 72: 903–910.

(List continued on next page.)

*Primary Examiner*—Robert L. Nasser
(74) *Attorney, Agent, or Firm*—Lyon & Lyon LLP

(57) ABSTRACT

A method for detecting optimal lung volume and determining the maximum lung compliance of a patient on high frequency oscillatory ventilation includes the steps of measuring the peak-to-peak oscillatory pressures in the proximal and distal ends of an endotracheal tube positioned within the patient. The oscillatory pressure ratio is calculated from the peak-to-peak oscillatory pressures in the proximal and distal ends. The mean airway pressure of the patient is then altered. The oscillatory pressure ratio is then recalculated at the altered mean airway pressure. The mean airway pressure is repeatedly altered while additional oscillatory pressure measurements are made until the oscillatory pressure ratio is at or near its minimum value.

27 Claims, 7 Drawing Sheets

OTHER PUBLICATIONS

McCann, E.M. et al., "Pulmonary Function in the Sick Newborn Infant", Ped. Res. (1987), 21: 313–325.

Edberg, K.E. et al., "Lung Volume, Gas Mixing, and Mechanics of Breathing in Mechanically Ventilated Very Low Birth Weight Infants with Idiopathic Respiratory Distress Syndrome", Ped. Res. (1991), 30: 496–500.

Vilstrup, C.T. et al., "Lung Volumes and Pressure–Volume Relations of the Respiratory System in Small Ventilated Neonates with Severe Respiratory Distress Syndrome", Ped. Res. (1996), 39: 127–133.

Pedley, T.J. et al., "Gas Flow and Mixing in the Airways", Critical Care Medicine (1994), 22: S24–S36.

Franken, H. et al., "Oscillating Flow of a Viscous Compressible Fluid through a Rigid Tube: a Theoretical Model", IEEE Trans. Biomed. Eng. (1981), 5: 416–420.

Byford, L.J. et al., "Lung Volume Recruitment During High–Frequency Oscillation in Atelectasis–prone Rabbits", J. Appl. Physiol. (1988), 64: 1607–1614.

McCulloch, P.R. et al., "Lung Volume Maintenance Prevents Lung Injury During High Frequency Oscillatory Ventilation in Surfactant–Deficient Rabbits", Am. Rev. Resp. Dis. (1988), 137: 1185–1192.

* cited by examiner

DEVICE AND METHOD FOR USING OSCILLATORY PRESSURE RATIO AS AN INDICATOR FOR LUNG OPENING DURING HIGH FREQUENCY OSCILLATORY VENTILATION

BACKGROUND OF THE INVENTION

A portion of the disclosure of this patent document may contain material which is subject to copyright protection. The copyright owner has no objection to the facsimile reproduction of the patent disclosure by any person as it appears in the Patent and Trademark Office patent files or records, but otherwise reserves all rights to the copyright whatsoever.

The invention relates generally to measurement of optimal lung volume during high frequency oscillatory ventilation of humans or other mammals. More particularly, this invention relates to the utilization of pressure measurements at the proximal and distal ends of an HFOV patient endotracheal tube as a proxy or indicator for optimal lung volume.

Frequently, a sick patient must be assisted in breathing by a ventilator. This patient may be human, or a non-human mammal. During conventional mechanical ventilation (CMV), the lung is inflated with a distending pressure called positive end inspiratory pressure (PIP). During HFOV, the lung is inflated with a continuous distending pressure called mean airway pressure ($\overline{P}_{aw}$). This mean airway pressure $\overline{P}_{aw}$ is superimposed with oscillating pressure variations.

In a diseased lung, some air sacs may collapse, preventing gas from entering or leaving and thereby preventing gas exchange through those air sacs. Because a fewer number of air sacs are available for gas exchange, the patient must be ventilated with a higher concentration of oxygen than normal to enable his or he remaining open air sacs to provide adequate blood oxygenation. While a high oxygen concentration is required to provide adequate blood oxygenation and keep the patient alive, it is also toxic.

During inflation of the lung with increasing PIP or $\overline{P}_{aw}$, the pressure increases and the collapsed air sacs of the lung begin to open, allowing them to once again take part in gas exchange. The pressure at which the air sacs begin to open is called the critical opening pressure. Air sacs opened because of ventilator inflation pressure are said to be recruited. As the number of recruited air sacs increases, the amount of oxygen that diffuses into the arterial blood also increases. This is reflected as an increase in blood oxygen saturation level, as may be non-invasively measured by pulse oximetry or directly with an arterial blood gas measurement. The increase in oxygen in the blood enables the caregiver to lower the inspired oxygen concentration toward less toxic levels. For these reasons, it is generally beneficial to recruit as many air sacs as possible in a patient undergoing ventilation.

In HFOV, when an increase in the ventilator mean airway pressure fails to improve the oxygen saturation level of the blood, the lung is considered to be recruited. If additional pressure is added to a stable lung, the patient runs the risk of experiencing overinflation. Overinflation significantly increases the chances for lesions to form in the lung tissue. Such lesions can allow air to leak into the space between the lungs and the chest wall, and can be lethal. In addition, overdistention also adversely affects pulmonary bloodflow.

If the lung has been pressurized to the point of overinflation during recruitment, the pressure can be reduced to alleviate overdistention. However, due to the elasticity of the lungs, which causes a nonlinear pressure/volume relationship which is different for inhalation than exhalation, the window between overdistention and lung collapse can be small. If the pressure is weaned too low, some alveoli will start to collapse. This pressure at which the air sacs begin to derecruit is called the critical closing pressure. Consequently, to prevent overinflation in a given patient, ventilator pressures must be reduced to a lower level to find the safest pressure with the air sacs recruited. Unfortunately, it is quite easy to bypass the window between overdistention and lung collapse. When a significant number of alveoli collapse, the patient's blood oxygen can fall to dangerously low levels. As can be seen, this trial and error method is risky for the ventilated patient.

Underinflation of the lung creates another set of physical problems. If the lung is underinflated, diseased lung tissue may be derecruited, causing a condition called atelectasis. That is, diseased air sacs that took part in gas exchange when the lung was properly inflated (i.e., air sacs that had been recruited) will no longer do so if the inflation pressure is too low. Those air sacs will close again, and no gas exchange will take place through them, inhibiting the patient's ability to absorb oxygen and jettison carbon dioxide. Underinflation thereby causes atelectasis, which may be a life-threatening condition. Finally, underinflation can result in the release of chemicals in the lung tissue that induce biochemical lung injury.

Given the dangers of overinflation and underinflation, the pressure output of a ventilator must be high enough to prevent underinflation, and low enough to prevent overinflation. In the case of HFOV, the mean airway pressure $\overline{P}_{aw}$ must fall in this rather narrow range between underinflation and overinflation.

During HFOV operation, it is desirable to achieve maximal lung recruitment and minimal overdistention. Unfortunately, $\overline{P}_{aw}$ is not, by itself, an indicator that can be used to determine when this point has been reached. There thus is a need for a relatively simple yet accurate method of determining the optimal lung volume for lung injury patients. A need also exists for a device that can be easily and safely adjusted to the optimal lung volume of the patient.

SUMMARY OF THE INVENTION

In a first aspect of the invention a method for determining the optimal lung volume for a patient on high frequency oscillatory ventilation includes the following steps. Initially, the peak-to-peak oscillatory pressures are measured in the proximal and distal ends of an endotracheal tube positioned within the patient. The oscillatory pressure ratio is then calculated from the peak-to-peak oscillatory pressures in the proximal and distal ends of the endotracheal tube. The mean airway pressure is altered and the oscillatory pressure ratio is recalculated at the altered mean airway pressure. The mean airway pressure is subsequently altered and the oscillatory pressure ratio is recalculated until the oscillatory pressure ratio is at or near its minimum value.

In a second aspect of the invention a method for determining the maximum lung compliance of a patient on high frequency oscillatory ventilation includes the following steps. Initially, the patient is provided with high frequency oscillatory ventilation at an initial mean airway pressure. Next, the peak-to-peak oscillatory pressures in the proximal and distal ends of an endotracheal tube positioned within the patient are measured. Based on these measurements, the oscillatory pressure ratio is calculated from the peak-to-peak oscillatory pressures in the proximal and distal ends of the endotracheal tube. The mean airway pressure provided to the patient is then increased. The oscillatory pressure ratio at the increased mean airway pressure is then calculated. The mean airway pressure is subsequently increased and the oscillatory pressure ratio recalculated until the oscillatory pressure ratio increases.

In a third aspect of the invention, the method according to the second aspect wherein the step of increasing the mean airway pressure is replaced by the step of decreasing the mean airway pressure.

In yet a forth aspect of the invention, a device for determining the maximum lung compliance of a patient on high frequency oscillatory ventilation includes a first pressure sensor at a proximal end of an endotracheal tube in the patient and a second pressure sensor at the distal end of the endotracheal tube. The device also includes means for calculating the oscillatory pressure ratio based on measurements obtained from the first and second pressure sensors. A mean airway pressure controller is provided for altering the mean airway pressure delivered to the patient. The device also includes a display for displaying the oscillatory pressure ratio.

It is an object of the invention to provide a method and device for determining the optimum mean airway pressure for maximal lung recruitment and minimal overdistention. The method and device is useful on patients with lung damage or lung disease. The method and device will also work with patients with healthy lungs. Generally, the method and device are useful in adult and pediatric patients with ARDS or acute lung injury. The method and device are particularly useful in newborn infants suffering from idiopathic respiratory distress syndrome (IRDS).

DETAILED DESCRIPTION OF THE PREFERRED EMBODIMENTS

Figure 1:
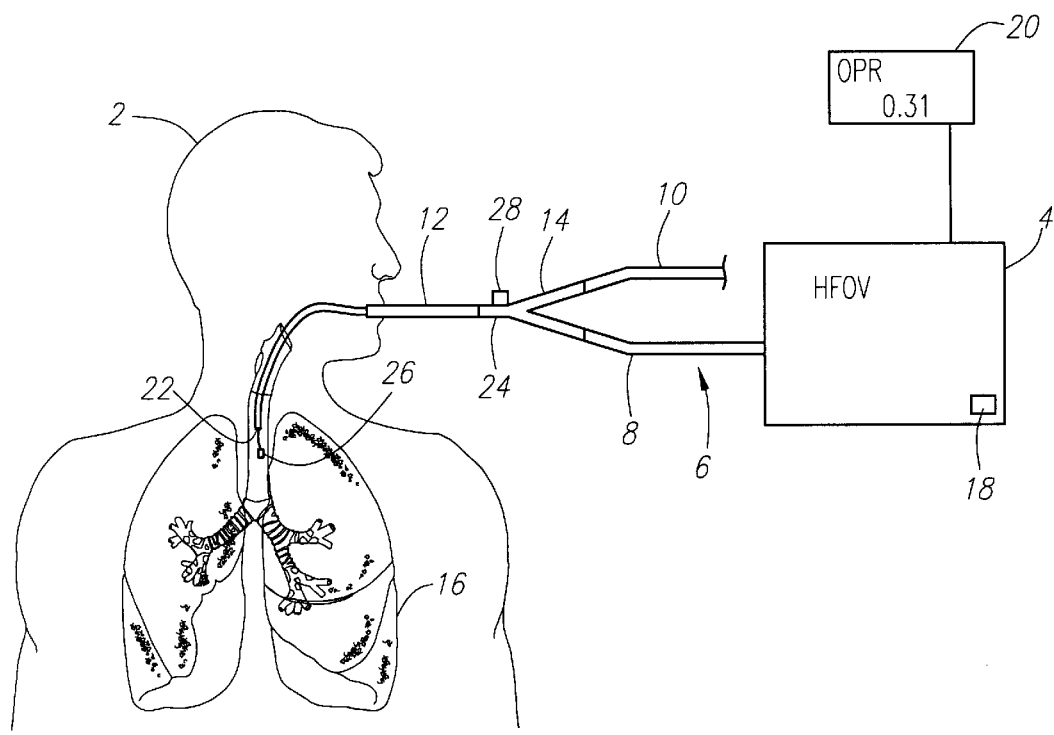
FIG. 1 is a schematic illustration of the high frequency oscillatory ventilator connected to a patient.

FIG. 1 illustrates a patient 2 connected to a high frequency oscillatory ventilator 4. High frequency oscillatory ventilators 4 are well known and have been previously described in, e.g., U.S. Pat. No. 4,719,910, which is incorporated by reference as if set forth fully herein. Unlike conventional ventilators that ventilate by positive-pressured gas flow and rely on passive recoil of the lung tissue for expiration, high frequency oscillatory ventilators 4 employ an active expiratory phase in which gas is pushed into and pulled out of a patient's 2 lungs 16 during alternate cycles of an oscillating diaphragm (or piston) of the high frequency oscillatory ventilator 4. Generally, the forward motion of the diaphragm (toward the patient 2) creates a positive-going pressure relative to the static pressure in the patient's 2 airway. As the diaphragm is driven rearward from its most forward position, the dynamic pressure it generates reverses from positive-going to negative-going. This bipolar dynamic pressure waveform is the principle reason for the success of the high frequency oscillatory ventilator 4 in providing improved respiratory gas exchange.

The high frequency oscillatory ventilator 4 includes a patient breathing circuit 6 that includes a inspiration limb 8 and an expiration limb 10. The inspiration limb 8 connects to an endotracheal tube 12 via a Y-piece 14. The endotracheal tube 12 is inserted into the patient's 2 airway during operation of the high frequency oscillatory ventilator 4. The breathing circuit 6 and endotracheal tube 12 are preferably made of standard flexible tubing that is used with ventilators.

During operation, the high frequency oscillatory ventilator 4 delivers a distending pressure called mean airway pressure $\overline{P}_{aw}$ to the patient's 2 lungs 16. Typically, the mean airway pressure $\overline{P}_{aw}$ is adjustable within the range of about 3 cm H$_2$O to about 55 cm H$_2$O. The mean airway pressure $\overline{P}_{aw}$ is superimposed with oscillating pressure (as seen, for example, in FIG. 3(b)). The oscillating pressure promotes gas exchange with the lungs 16. The oscillating pressure waves can take on many shapes including square, sinusoidal, triangular, ramp, and the like. It will be understood to those skilled in the art that present invention can be employed with any number of wave profiles used with HFOV devices. Typically, the oscillating pressure is set within the range of about 0 to about 90 cm H$_2$O above and below the mean airway pressure $\overline{P}_{aw}$. Preferably, the oscillating pressure also has a set frequency that is preprogrammed or manually adjusted on the high frequency oscillatory ventilator 4. Typically, the frequency is set approximate range of about 3 Hz to about 15 Hz. Preferably, the oscillating pressures and the oscillating frequency can be set by the operator of the high frequency oscillatory ventilator 4. The high frequency oscillatory ventilator 4 also preferably has an mean airway pressure control 18 that can either increase or decrease the mean airway pressure $\overline{P}_{aw}$ delivered to the patient 2.

Preferably, the high frequency oscillating ventilator 4 includes an adjustable I:E ratio, which generally falls within the approximate range of about 30% to about 50%. In addition, the high frequency oscillating ventilator 4 preferably includes adjustable bias flow. Generally, the bias flow is set within the approximate range of about 0 to about 60 liters/minute (LPM).

The high frequency oscillatory ventilator 4 preferably has a display unit 20 that can display the calculated oscillatory pressure ratio (OPR). While not mandatory, this display unit 20 can display additional information such as oscillatory frequency, mean airway pressure $\overline{P}_{aw}$, oscillating amplitude, gas concentrations, distal pressure readings, proximal pressure readings, % inspiration time, piston position and displacement, bias flow and the like. The display unit 20 can be a computer monitor, LCD screen, or the like.

The present OPR device and method can be incorporated into existing HFOV devices. For example, the OPR feature can be included on SensorMedics 3100 A and 3100 B model devices available from SensorMedics, 22705 Savi Ranch Parkway, Yorba Linda, Calif. 92887.

The endotracheal tube 12 of the high frequency oscillatory ventilator 4 has two ends—a distal end 22 that is positioned within the patient's 2 airway and a proximal end 24 that is located at the Y-piece 14. A first pressure sensor 26 is preferably located just beyond the distal end 22 of the endotracheal tube 12. Preferably, the first pressure sensor 26 extends a few millimeters beyond the distal end 22. Nonetheless, the first pressure sensor 26 is still referred to as being disposed at the distal end 22 of the endotracheal tube 12. A second pressure sensor 28 is located in the proximal end 24 of the endotracheal tube 12. Preferably, the pressure sensors 26, 28 are pressure transducers. The pressure sensors 26, 28 are sufficiently sensitive such that they can measure the peak-to-peak pressure readings within the endotracheal tube 12.

Figure 2:
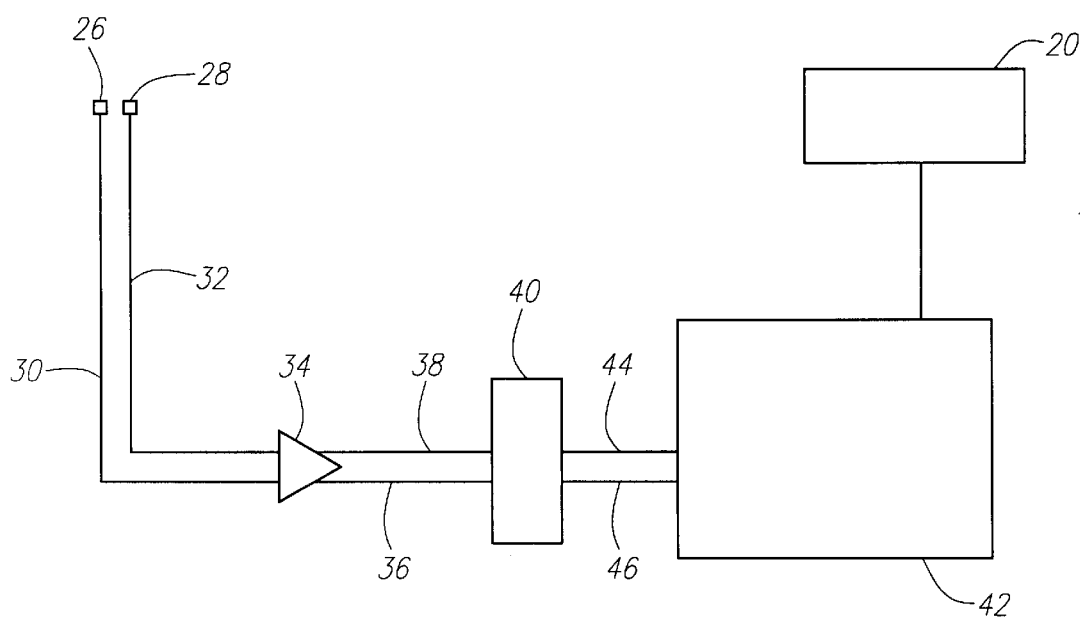
FIG. 2 illustrates the measurement and calculating system according to one aspect of the invention.
Figure 3A:
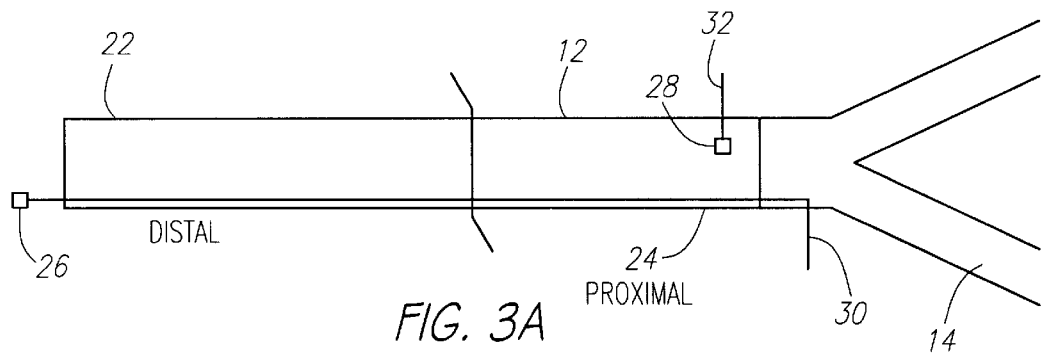
FIG. 3(a) illustrates the endotracheal tube including distal and proximal pressure sensors.

As seen in FIGS. 2 and 3(a), the pressure sensors 26, 28 are connected to signal lines 30, 32, respectively that report to the high frequency oscillatory ventilator 4. Preferably, the signal lines 30, 32 connect to an amplifier 34 that amplifies the signals from the pressure sensors 26, 28. The output of the amplifier 34 is passed via signal lines 36, 38 to peak/valley detector 40. The peak/valley detector 40 discriminates the maxima and minima of the superimposed pressure oscillations. This information is then passed to a microprocessor 42 via signal lines 44, 46. The microprocessor 42 calculates the OPR and displays the value on the display unit 20. OPR is defined as the ratio of the peak-to-peak oscillatory pressure at the distal end 22 of the endotracheal tube 12 to the peak-to-peak oscillatory pressure at the proximal end 24 of the endotracheal tube 12. As shown in more detail below, it has been found that OPR can be used as a proxy or indicator for maximal lung recruitment and minimal overdistention.

Figure 3B:
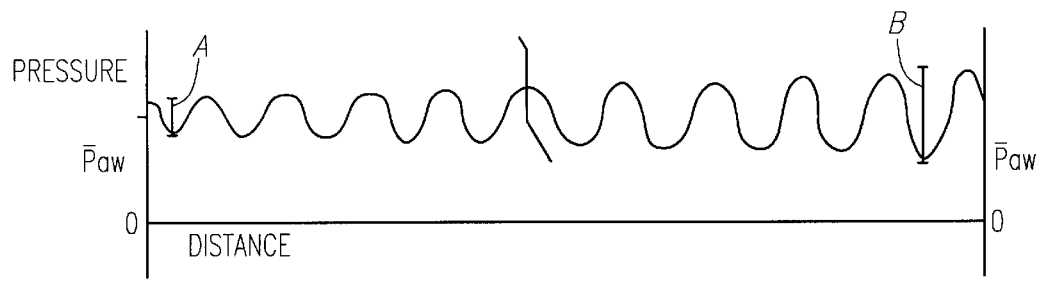
FIG. 3(b) illustrates the mean airway pressure and oscillatory pressure within the endotracheal tube of FIG. 3(a).

Referring now to FIGS. 3(a) and 3(b), FIG. 3(a) illustrates the endotracheal tube 12 including the distal and proximal ends 22, 24. FIG. 3(b), shown above FIG. 3(a), schematically illustrates the pressure profile within the endotracheal tube 12. As seen in FIG. 3(b), the pressure generally oscillates around the mean airway pressure $\overline{P}_{aw}$. The mean airway pressure is shown as a constant in FIG. 3(b). The pressure oscillations preferably have a fixed frequency although, it is possible to adjust this frequency. The pressure oscillations shown in FIG. 3(b) are somewhat exaggerated for ease of clarity. As seen in FIG. 3(b), the pressure oscillations are more extreme at the proximal end 24 of the endotracheal tube 12 than at the distal end 22 of the endotracheal tube 12. This reduction in pressure amplitude is generally caused by the dampening effect of the endotracheal tube 12 and the respiratory compliance of the patient 2. The magnitude of the pressure oscillations at the distal and proximate ends 22, 24 is preferably quantified with peak-to-peak measurements taken by pressure sensors 26, 28. The peak-to-peak measurements at the distal and proximal ends 22, 24 are shown as distances A and B respectively on FIG. 3(b). The peak-to-peak distance is smaller at the distal end 22 of the endotracheal tube 12 than the peak-to-peak distance at the proximal end 24 of the endotracheal tube 12. The OPR, which is the peak-to-peak distance at the distal end 22 of the endotracheal tube 12 divided by the peak-to-peak distance at the proximal end 24 of the endotracheal tube 12 is a fractional number in this example. By taking peak-to-peak measurements at the distal and proximal ends 22, 24 of the endotracheal tube 12 using pressure sensors 26, 28, it is possible to calculate an OPR value for each peak-to-peak measurement. As been stated previously, it has been discovered that when the OPR value reaches its minimum value, lung recruitment is at its maximum. In addition, at the minimum OPR value, overdistention is minimal.

The measurement of the peak-to-peak oscillatory pressures in the distal and proximal ends 22, 24 can be done on a periodic basis, or alternatively, can be done on a continuous basis.

Figure 14:
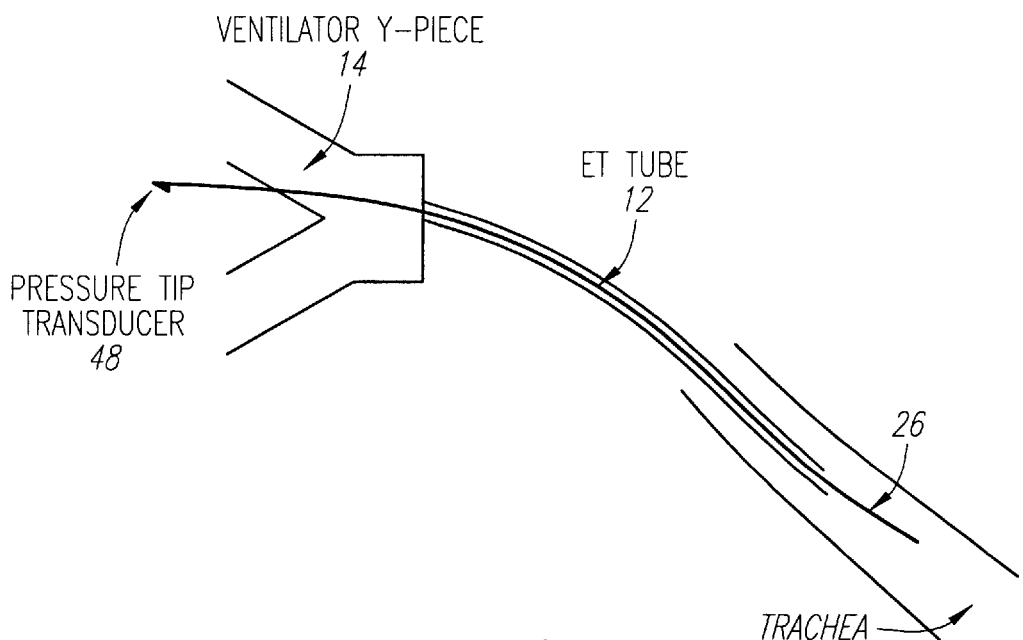
FIG. 14 schematically illustrates an alternative embodiment using only a single pressure sensor to measure the oscillatory pressure ratio OPR.

In another aspect of the invention, as seen in FIG. 14, a single pressure sensor (either 26 or 28 but referred to as 26 for clarity) is used. In this aspect of the invention, the pressure sensor 26 is moveable between the distal end and proximal ends 22, 24 of the endotracheal tube 12. This can be done on a catheter-type pressure tip transducer 48 with a pressure sensor 26 located at a distal end thereof. The pressure sensor tip transducer 48 is moved axially between proximal and distal portions for two consecutive measurements, which will give an intermittent OPR value. The movement of the pressure tip transducer 48 is preferably done manually.

Figure 4:
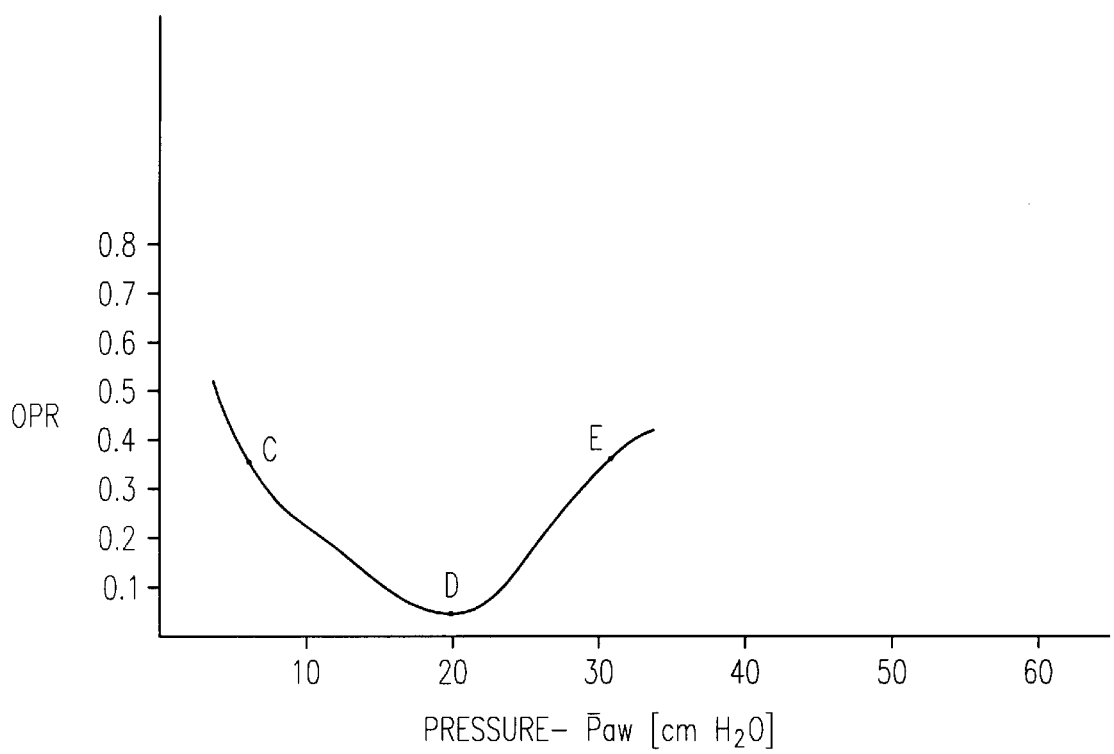
FIG. 4 illustrates a graph of mean airway pressure $\overline{P}_{aw}$ as a function of oscillatory pressure ratio OPR.

FIG. 4 illustrates a simulated graph illustrating the OPR value versus mean airway pressure $\overline{P}_{aw}$ for a patient 2 using a high frequency oscillatory ventilator 4. At low pressures, for example, around 5 cm $H_2O$ (point C on FIG. 4), the OPR value is relatively high at around 0.38. Similarly, at high pressures, for example, around 30 cm $H_2O$) (point E on FIG. 4), the OPR value is relatively high at around 0.35. At point D in FIG. 4, the OPR reaches its minimum value at about 0.05. Point D is the optimum mean airway pressure $\overline{P}_{aw}$ for this patient 2 since OPR is at its minimum. In operation, the health care provider typically alters the mean airway pressure $\overline{P}_{aw}$ until this point is reached.

In one embodiment of the invention, during operation of the high frequency oscillatory ventilator 4, the patient 2 is initially prescribed a low level of mean airway pressure $\overline{P}_{aw}$, for example, point C on FIG. 4. The health care provider or other trained professional then reads the OPR value from the display unit 20. After this initial reading, the mean airway pressure $\overline{P}_{aw}$ is then increased from its original value using the mean airway pressure controller 18 and the OPR value is read again from the display unit 20. The OPR value should drop from its initial value as lung recruitment increases. The mean airway pressure is increased further and additional OPR readings are taken. This process of increasing the mean airway pressure and reading OPR values is repeated until the minimum OPR value is reached. Typically, the operator continues to increase the mean airway pressure $\overline{P}_{aw}$ until the OPR value begins to increase. The increase in OPR indicates that the minimum OPR value has been passed. The operator of the high frequency oscillatory ventilator 4 can then fine-tune the mean airway pressure until the minimum OPR is achieved.

In another aspect of the invention, the patient 2 is initially prescribed a high level of mean airway pressure $\overline{P}_{aw}$, for example, point E on FIG. 4. The health care provider or other trained professional then reads the OPR value from the display unit 20. After this initial reading, the mean airway pressure $\overline{P}_{aw}$ is then decreased from its original value using the mean airway pressure controller 18 and the OPR value is read again from the display unit 20. The OPR value should drop from its initial value as lung compliance increases. The mean airway pressure is decreased further and additional OPR readings are taken. This process of decreasing the mean airway pressure and reading OPR values is repeated until the minimum OPR value is reached. Typically, the operator continues to decrease the mean airway pressure $\overline{P}_{aw}$ until the OPR value begins to increase. The increase in OPR indicates that the minimum OPR value has been passed. The operator of the high frequency oscillatory ventilator 4 can then fine-tune the mean airway pressure until the minimum OPR is achieved.

Generally, the operator of the high frequency oscillatory ventilator 4 alters the mean airway pressure $\overline{P}_{aw}$ incrementally. This gives the patient 2 and the sensors 26, 28 a chance to reach steady state or semi-steady state values. In this regard the mean airway pressure is controlled manually by the high frequency oscillatory ventilator 4 operator.

In another aspect of the invention, the mean airway pressure of the high frequency oscillatory ventilator 4 is controlled automatically. In this embodiment, the microprocessor 42 sends signals to control the mean airway pressure controller 18. The operation of the high frequency oscillating ventilator 4 in this manner would occur, however, in the same general manner is in the manual operation, i.e., repeated measurements of OPR and modification of the mean airway pressure. A feedback loop arrangement could also be employed. In addition, the alteration of the mean airway pressure and the OPR readings could be performed on a continuous or near continuous basis.

While it is preferable that the microprocessor 42 perform the OPR calculation, it is within the scope of the invention to eliminate the microprocessor 42 as a means for calculating OPR. For example, OPR values can be calculated manually by an operator or other person using a computational device such as a calculator, or alternatively, by performing the calculation by hand.

Generally, once the minimum OPR value is reached it is preferable to slightly reduce the $\overline{P}_{aw}$. Slight reduction in $\overline{P}_{aw}$ reduces the chance of overdistention of the lungs. In addition, once the lung is fully recruited (minimum OPR), the alveoli are open and will stay open even at lower $\overline{P}_{aw}$ due to the hysteresis nature of alveoli inflation/collapse. By slightly reducing $\overline{P}_{aw}$, pulmonary blood vessel resistance is reduced thereby improving blood flow and hence gas exchange in the lung. If the $\overline{P}_{aw}$ is reduced too much, alveoli will collapse. By monitoring OPR, however, this point can be determined, since OPR will begin to increase when the alveoli starts to collapse.

EXPERIMENTAL MODELING

Figure 5:
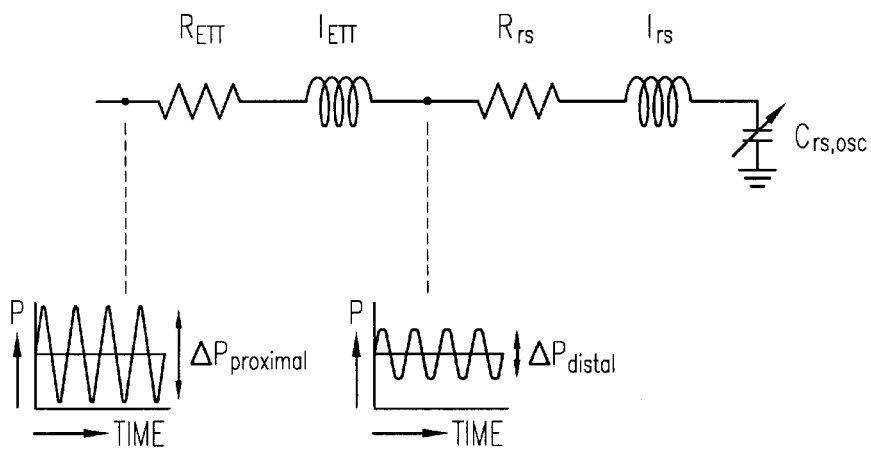
FIG. 5 illustrates an electrical analog model of the endotracheal tube and the respiratory system.

A mathematical model was developed for the endotracheal tube and respiratory system of a neonate suffering from IRDS. In its most general sense, the model consisted of linear viscous and inertive elements and a non-linear compliance allowing for alveolar recruitment and overdistention. An electrical analog model, as shown in FIG. 5, was used to simulate the mechanical characteristics of the respiratory system including the endotracheal tube. Viscous losses in the endotracheal tube and airways were represented by resistors ($R_{ETT}$ and $R_{rs}$). Inertive loads of the endotracheal tube and airways were represented by inductors ($I_{ETT}$ and $I_{rs}$). A variable capacitor ($C_{rs,\ osc}$) simulated respiratory system compliance during HFOV, i.e., under the condition of small alveolar pressure amplitudes.

The following are a list of abbreviations used throughout: $C_{alv}$=compliance of a single, open alveolus; $C_{rs}$=respiratory system compliance; $C_{rs,\ osc}$=respiratory system compliance during high frequency oscillatory ventilation; ETT= endotracheal tube; $I_{ETT}$=ETT inertance; $I_{rs}$=respiratory system inertance; IRDS=idiopathic respiratory distress syndrome; $N_{recr}$=number of recruited alveoli; OPR=oscillatory pressure ratio; $OPR_{min}$=minimum OPR; $\overline{P}_{aw}$=mean airway pressure; $\Delta P_{distal}$=peak-to-peak oscillatory pressure at the distal end of the ETT; $\Delta P_{proximal}$=peak-to-peak oscillatory pressure at the proximal end of the ETT; $R_{ETT}$=ETT resistance; $R_{rs}$=respiratory system resistance; $V_{alv}$=volume of single alveolus; $V_0$=volume of an open alveolus at ambient pressure; V'=flow rate.

Figure 6:
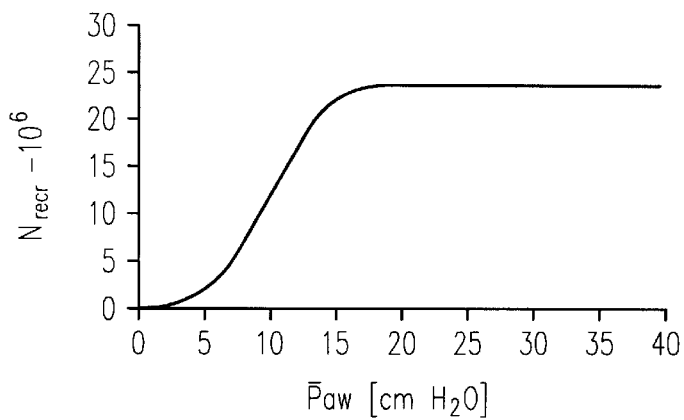
FIG. 6 is a graph illustrating the mean airway pressure $\overline{P}_{aw}$ as a function of the number of recruited alveoli $N_{recr}$.

Respiratory system compliance $C_{rs,\ osc}$ was assumed to be mainly dependent on lung compliance and airway distensibility and chest wall compliance Were assumed negligible. Lung compliance consisted of two components, one depending on the extension of alveoli and the other on the recruitment of alveoli, as described by Venegas and Fredberg. See Venegas J G, Fredberg J J. Understanding the pressure cost of ventilation: why does high-frequency ventilation work? Critical Care Medicine, 1994; 22: S49–S57. In neonatal IRDS, alveolar regions are collapsed due to a lack of surfactant. In the present model it was assumed that alveoli are either open or completely closed dependent on the mean alveolar distending pressure. In addition, it was assumed that the number of recruited alveoli $N_{recr}$ did not vary within a respiratory cycle during HFOV. Opening pressures of individual alveoli were taken to be normally distributed with a mean of 10 cm $H_2O$ and a standard deviation of 4 cm $H_2O$ as shown in FIG. 6.

Figure 7:
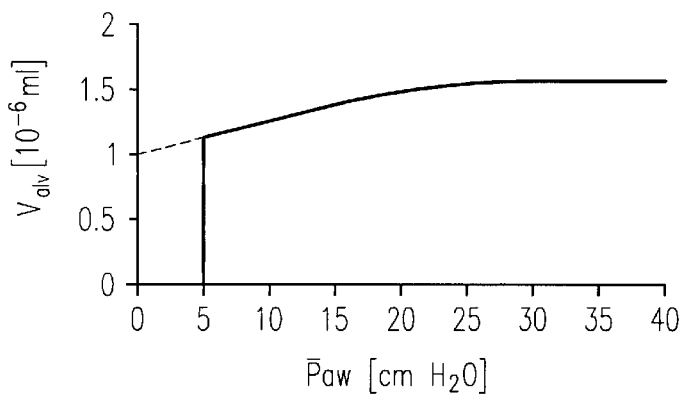
FIG. 7 is a graph illustrating the mean airway pressure $\overline{P}_{aw}$ as a function of single alveolus volume $V_{alv}$ with an opening pressure of 5 cmH$_2$O, a linear alveolar compliance of $2.5 \times 10^{31\ 8}$ ml·cmH$_2$O$^{-1}$ and overdistention above 20 cmH$_2$O.

The relationship between distending pressure and volume of an alveolus (FIG. 7) was linear above it's opening pressure and below 20 cm $H_2O$ and non-linear above 20 cm $H_2O$ (with $C_{alv}$ the alveolar respiratory compliance and $V_0$ the alveolar volume of an open alveolus at zero pressure). The following formulas represent $V_{alv}$ for different values of $\overline{P}_{aw}$.

$$V_{alv}=0 \text{ for } \overline{P}_{aw} \leq P_{open} \quad (1)$$

$$V_{alv}=\overline{P}_{aw}*C_{alv}+V_0 \text{ for } P_{open} \leq \overline{P}_{aw} \leq 20 \text{ cm } H_2O \quad (2)$$

$$V_{alv} = 20*C_{alv}*\left[\frac{3}{2}-\frac{1}{2}*\exp\left(\frac{-(\overline{P}_{aw}-20)}{10}\right)\right]+V_0 \text{ for } \overline{P}_{aw} > 20 \text{ cm } H_2O \quad (3)$$

Figure 8:
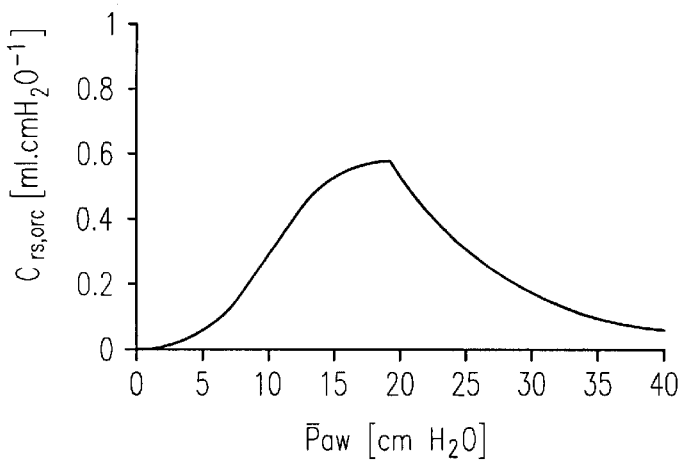
FIG. 8 is a graph illustrating the mean airway pressure $\overline{P}_{aw}$ as a function of the resultant respiratory compliance $C_{rs,\ osc}$ on HFOV.

Respiratory compliance as a function of pressure (FIG. 8) was derived by multiplying the number of recruited alveoli $N_{recr}$ with the compliance of open alveoli, the latter being approximated by $dV_{alv}/d\overline{P}_{aw}$.

The viscous losses and inertive loads were assumed to be independent of distending pressure. The resistance $R_{ETT}$ of a 3 mm diameter ETT was assumed to be flow dependent and approximated by $R_{ETT}=k_1+k_2 \cdot |V'|$ where V' is the flow rate and $k_1=30$ cm $H_2O \cdot s \cdot L^{-1}$ and $k_2=350$ cm $H_2O \cdot s^2 \cdot L^{-2}$. Tube inertance was calculated according to the following formula:

$$I=\rho \cdot L \cdot A^{-1} \text{ (where } \rho\text{=air density; L=tube length, A=tube cross sectional area) which yields } I_{ETT}=0.3 \text{ cm } H_2O \cdot s^{-2} \cdot L^{-1}. \quad (4)$$

The model was implemented and dynamically simulated in Matlab (MathWorks Inc., Natick Mass., USA). The respiratory system was subjected to a sinusoidal oscillatory pressure with a peak-to-peak value of $\Delta P_{proximal}$ at the proximal opening of the ETT. The oscillatory pressure at the distal end ($\Delta P_{distal}$) was also determined. To relate the distal to proximal oscillations, the oscillatory pressure ratio was defined as $\Delta P_{distal}/\Delta P_{proximal}$.

Values for the respiratory variables were adopted from the work of Dorkin et al. who applied the Forced Oscillation Technique in four neonates with IRDS (table 1 below). See Dorkin H L, Stark A R, Werthammer J W, Strieder D J, Fredberg J J, Frantz I D, Respiratory system impedance from 4 to 40 Hz in paralyzed intubated infants with respiratory disease. Journal of Clinical Investigation, 1983; 72: 903–910. $C_{alv}$ in the model was set to the $C_{rs}$ obtained in the Dorkin et al. study divided by the estimated total number of alveoli $N_{total}$, which was approximately 24 million. $V_0$, the average volume of a single alveolus at ambient pressure, was set to 25 ml divided by $N_{total}$. A number of simulations and calculations were then run. The relationship between $C_{rs,\ osc}$ and OPR was determined for each subject at an oscillatory frequency of 10 Hz and a $\Delta P_{proximal}$ of 20 cm $H_2O$. For each subject, OPR was calculated as a function of $\overline{P}_{aw}$ in 1 cm $H_2O$ increments. Using subject B, run number two was repeated oscillatory frequency set at 8, 10, 12, and 15 Hz. Using subject B, run number two was repeated with $\Delta P_{proximal}$ set at 10, 15, 20, and 25 cm $H_2O$. Using subject B, run number two was repeated and tube resistance $R_{ETT}$ was increased with consecutively 25%, 50%, and 75%. In simulations two through five, the minimum OPR value ($OPR_{min}$) as well as the $\overline{P}_{aw}$ at which $OPR_{min}$ occurred were determined.

TABLE 1

| Subject | $R_{rs}$ (cmH$_2$O.s.L$^{-1}$) | $C_{rs}$ (ml.cmH$_2$O$^{-1}$) | $I_{rs}$ (cmH$_2$O.s$^2$.L$^{-1}$) |
|---|---|---|---|
| A | 34 | 0.22 | 0.0056 |
| B | 29 | 0.39 | 0.018 |
| E | 33 | 0.28 | 0.047 |
| F | 22 | 0.68 | 0.028 |

Table 1. Respiratory variables in four neonates with IRDS $C_{rs}$=respiratory system compliance; $R_{rs}$=resistance; $I_{rs}$=inertance. (Subjects C and D in their study were not intubated). Variables were found by Dorkin et al. See Dorkin H L, Stark A R, Werthammer J W, Strieder D J, Fredberg J J, Frantz I D, Respiratory system impedance from 4 to 40 Hz in paralyzed intubated infants with respiratory disease. Journal of Clinical Investigation, 1983; 72: 903–910.

To investigate the sensitivity of the relationship between $\overline{P}_{aw}$ and OPR for the different physical characteristics of the lungs, the model was fed with a wide range of different respiratory variables. Starting with the nominal variables of table 2 (shown below), alternatively, each variable was set to its extreme value. This was repeated with two variables set at an extreme value. This was repeated with two variables set an extreme value, then tree variables, and so on and so forth, yielding a total of eighty-one combinations. For each permutation the relationship between $\overline{P}_{aw}$ and OPR, $OPR_{min}$ and the $\overline{P}_{aw}$ at which $OPR_{min}$ occurred were determined.

TABLE 2

| Variable | nominal | minimum | maximum |
|---|---|---|---|
| $R_{rs}$ (cmH$_2$O.s.L$^{-1}$) | 50 | 20 | 200 |
| $C_{rs}$ (ml.cmH$_2$O$^{-1}$.kg$^{-1}$) | 0.6 | 0.2 | 2 |
| $I_{rs}$ (cmH$_2$O.s$^2$.L$^{-1}$) | 0.025 | 0.005 | 0.05 |
| f(Hz) | 10 | 5 | 15 |

Table 2. Neonatal respiratory variables: $C_{rs}$=respiratory system compliance; $R_{rs}$=resistance; $I_{rs}$=inertance; f=oscillatory frequency. In the model a body weight of 1.5 kg was assumed.

Figure 9:
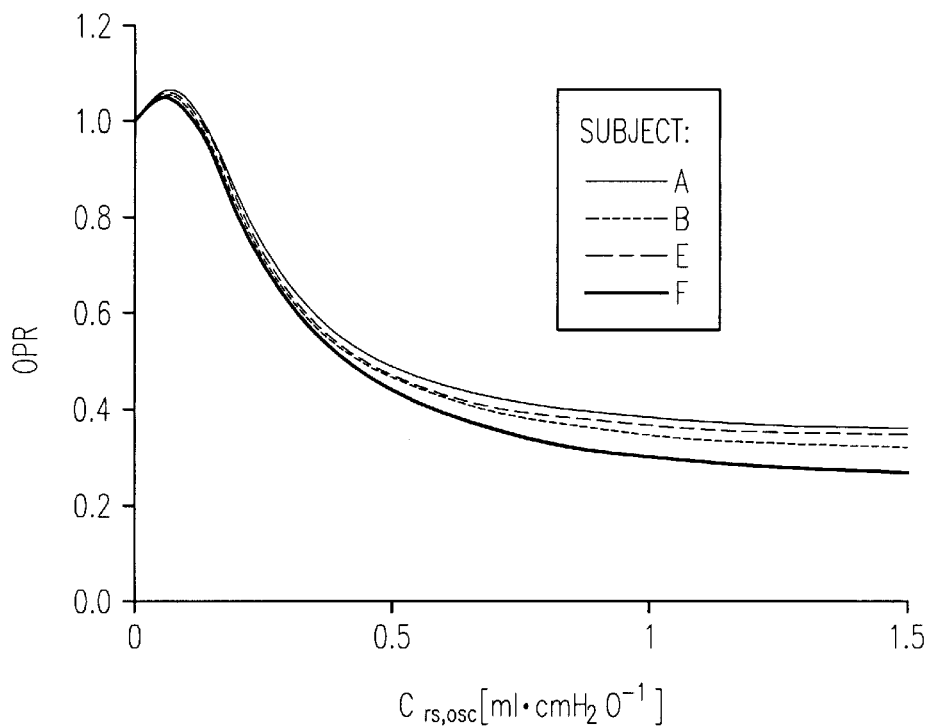
FIG. 9 is a graph illustrating the oscillatory pressure ratio OPR as a function of respiratory compliance $C_{rs,\ osc}$.

The relationship between $C_{rs,\ osc}$ and OPR for the four subjects at an oscillatory frequency of 10 Hz is shown in FIG. 9. All curves have a similar shape. In the range of small values of $C_{rs,\ osc}$ the OPR is far larger than unity implying an amplification of pressure oscillations. At $C_{rs,\ osc}$ larger than 0.08 ml·cmH$_2$O$^{-1}$ the OPR decreases with increasing $C_{rs,osc}$.

Figure 10:
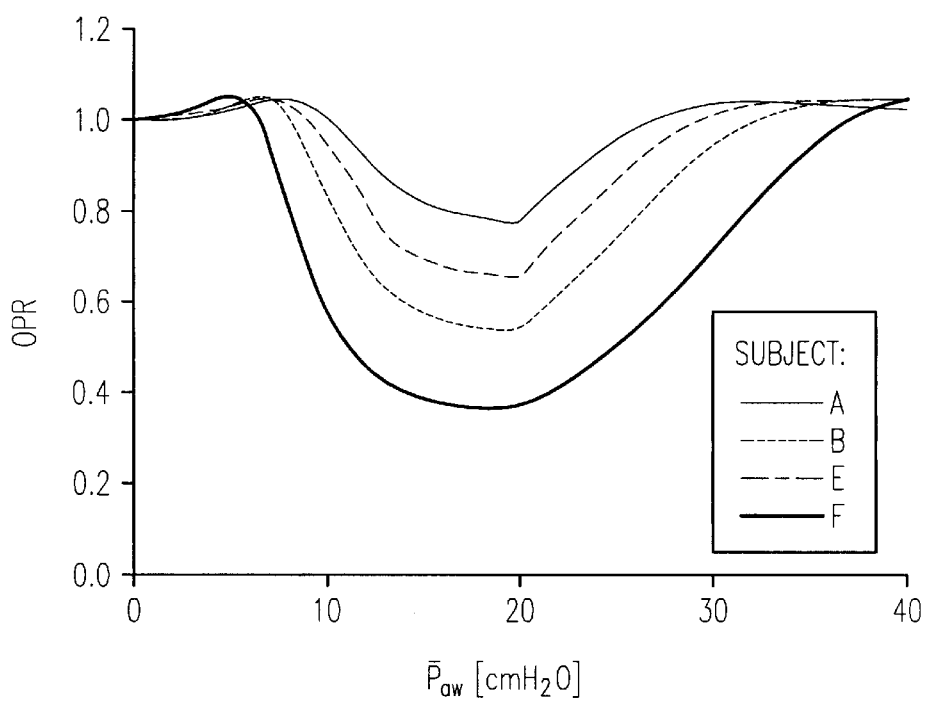
FIG. 10 is a graph illustrating the oscillatory pressure ratio OPR as a function of mean airway pressure $\overline{P}_{aw}$ for subjects A, B, E, and F from Table 1.

The relationship between $\overline{P}_{aw}$ and OPR for the four subjects of table 1 is shown in FIG. 10. All curves have a distinct minimum (range of $OPR_{min}$=0.37–0.78) which was reached at a $\overline{P}_{aw}$ of 20 cmH$_2$O ($\overline{P}_{aw20}$). Variation of oscillatory frequency, $\Delta P_{proximal}$, and $R_{ETT}$ led to a similar global relationship between $\overline{P}_{aw}$ and OPR with the minimum at $\overline{P}_{aw20}$. See FIGS. 11 through 13. The obtained OPR and $OPR_{min}$, however, were dependent on frequency, $\Delta P_{proximal}$ and $R_{ETT}$. For the eighty-one permutations of respiratory variables, the $OPR_{min}$ was 0.60±0.23. In all cases this minimum was reached at $\overline{P}_{aw20}$.

The simulated respiratory compliance was dependent on distending pressure as is typically seen in neonatal IRDS. At low $\overline{P}_{aw}$ compliance is low when a large part of the lungs is atelectatic. At increasing $\overline{P}_{aw}$ compliance increases when lung volume is gradually recruited. Above a $\overline{P}_{aw}$ of 20 cmH$_2$O the lungs are nearly completely recruited and volume increase occurs by alveolar (over) distention concomitant with a decrease of compliance. To simplify the model, resistance and inertance were insensitive to changes in lung volume.

Figure 11:
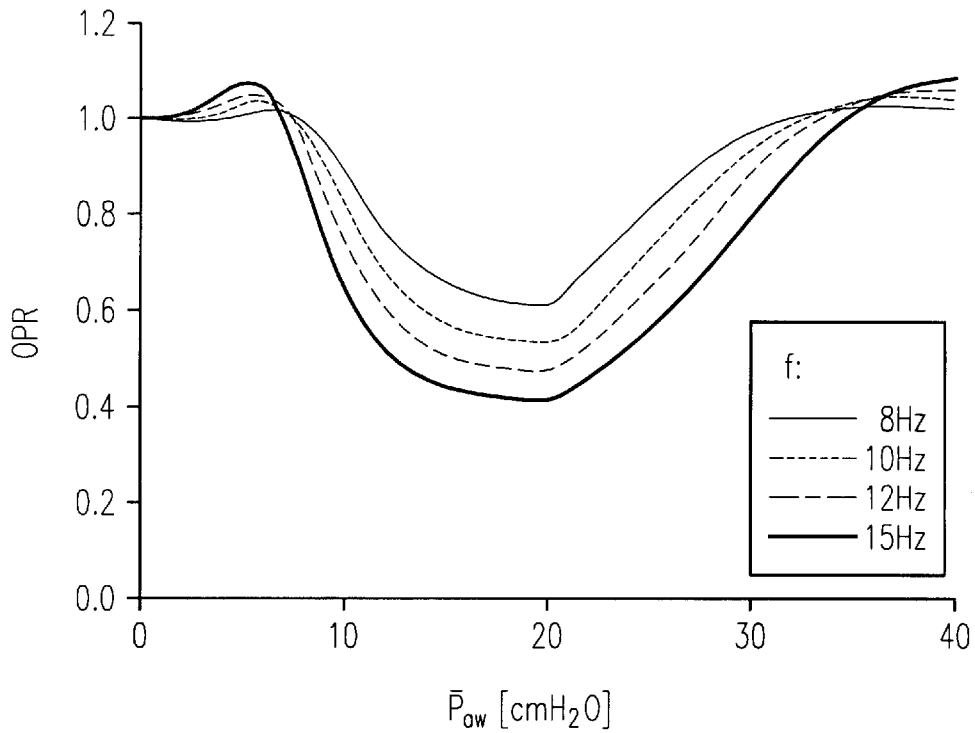
FIG. 11 is a graph illustrating the oscillatory pressure ratio OPR as a function of mean airway pressure $\overline{P}_{aw}$ four different oscillatory frequencies using subject B from Table 1.
Figure 12:
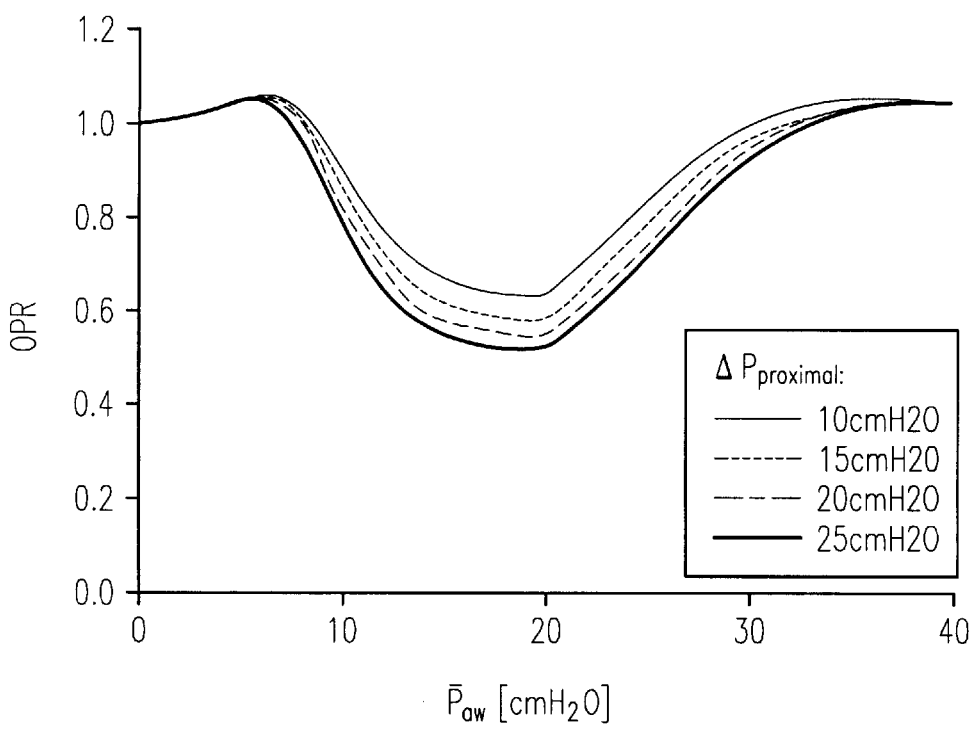
FIG. 12 is a graph illustrating the oscillatory pressure ratio OPR as a function of mean airway pressure $\overline{P}_{aw}$ a four different settings of $\Delta P_{proximal}$ using subject B from Table 1.
Figure 13:
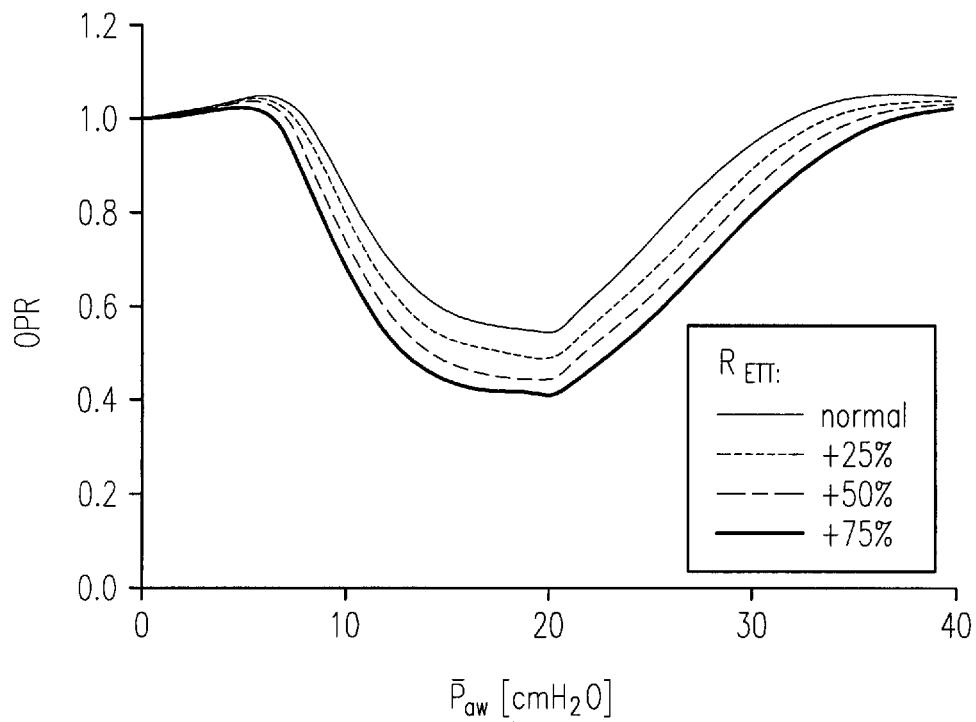
FIG. 13 is a graph illustrating the oscillatory pressure ratio OPR as a function of mean airway pressure $\overline{P}_{aw}$ a four different settings of $R_{ETT}$ using subject B from Table 1.

In order to describe the relationship between the proximal and distal oscillatory pressures, a variable, OPR (the Oscillatory Pressure Ratio) was defined. Investigation of OPR as a function of respiratory compliance (FIG. 9) revealed that OPR decreased at increasing compliance, except for very low compliances, below 0.08 ml·cmH$_2$O$^{-1}$. Using the respiratory variables of four patients in the model, it had been demonstrated that OPR is minimal when compliance is maximal, at a $\overline{P}_{aw}$ of 20 cmH$_2$O (FIG. 10). The $OPR_{min}$ obtained in the mathematical model (0.37–0.78) was higher compared to values described in the literature (0.03–0.47). The difference may be explained by the fact that the mechanical properties of both the ETT and the respiratory system were not determined using both the large amplitudes and high frequencies used during HFOV. When simulations were carried out at different oscillatory frequencies, the minimum OPR was reached at the same $\overline{P}_{aw}$ independent of frequency (as seen in FIG. 11). However, the value of $OPR_{min}$ was frequency dependent. Similar results were found when $\Delta P_{proximal}$ was varied (as seen in FIG. 12). This indicates a frequency and amplitude dependence of the OPR-$\overline{P}_{aw}$ relationship. This is important for OPR interpretation as these ventilatory parameters may be changed during the clinical application of HFOV. The OPR-$\overline{P}_{aw}$ relationship depends in a similar way on ETT resistance. Since in clinical practice the ETT may become partially blocked by mucus, this aspect is particularly important for correct OPR interpretation.

To investigate the sensitivity of various parameters in response to respiratory mechanics, eighty one permutations of respiratory variables were input into the model at nominal and extreme values. In all cases the $OPR_{min}$ was reached at the $\overline{P}_{aw20}$ when compliance was maximal. It was found that OPR reached a minimum at maximal lung compliance, which also corresponds to the transition between maximal lung recruitment and minimal overdistention.

While embodiments of the present invention have been shown and described, various modifications may be made without departing from the scope of the present invention. The invention, therefore, should not be limited, except to the following claims, and their equivalents.

What is claimed is:

1. A method of determining the optimum mean airway pressure for a patient on high frequency oscillatory ventilation comprising the steps of:
   (a) measuring the peak-to-peak oscillatory pressures in the proximal and distal ends of an endotracheal tube positioned within the patient;
   (b) calculating the oscillatory pressure ratio from the peak-to-peak oscillatory pressures in the proximal and distal ends of the endotracheal tube;
   (c) altering the mean airway pressure to the patient;
   (d) recalculating the oscillatory pressure ratio at the altered mean airway pressure; and
   (e) repeating steps (c) and (d) until the oscillatory pressure ratio is at or near its minimum value.

2. The method according to claim 1, wherein the step of altering the mean airway pressure is accomplished by decreasing the mean airway pressure.

3. The method according to claim 1, wherein the step of altering the mean airway pressure is accomplished by increasing the mean airway pressure.

4. The method according to claim 1, wherein the measuring of the peak-to-peak oscillatory pressures in the proximal and distal ends is done on a periodic basis.

5. The method according to claim 1, wherein the measuring of the peak-to-peak oscillatory pressures in the proximal and distal ends is done on a continuous basis.

6. The method according to claim 1, further comprising the step of displaying the oscillatory pressure ratio on a display device.

7. The method according to claim 1, further comprising the step of altering the oscillatory frequency after the oscillatory pressure ratio is at or near its minimum value.

8. A method for determining the optimum mean airway pressure for a patient on high frequency oscillatory ventilation comprising the steps of:
   (a) providing the patient with high frequency oscillatory ventilation at an initial mean airway pressure;
   (b) measuring the peak-to-peak oscillatory pressures in the proximal and distal ends of an endotracheal tube positioned within the patient;
   (c) calculating the oscillatory pressure ratio from the peak-to-peak oscillatory pressures in the proximal and distal ends of the endotracheal tube;
   (d) increasing the mean airway pressure provided to the patient;
   (e) recalculating the oscillatory pressure ratio at the increased mean airway pressure;
   (f) repeating steps (d) and (e) until the oscillatory pressure ratio increases.

9. The method according to claim 8, further comprising the step of altering the mean airway pressure until the oscillatory pressure ratio is at or near its minimum value.

10. The method according to claim 8, wherein the measuring of the peak-to-peak oscillatory pressures in the proximal and distal ends is done on a periodic basis.

11. The method according to claim 8, wherein the measuring of the peak-to-peak oscillatory pressures in the proximal and distal ends is done on a continuous basis.

12. The method according to claim 8, further comprising the step of displaying the oscillatory pressure ratio on a display device.

13. The method according to claim 8, further comprising the step of altering the oscillatory frequency after the oscillatory pressure ratio is at or near its minimum value.

14. A method for determining the optimum mean airway pressure for a patient on high frequency oscillatory ventilation comprising the steps of:
   (a) providing the patient with high frequency oscillatory ventilation at an initial mean airway pressure;
   (b) measuring the peak-to-peak oscillatory pressures in the proximal and distal ends of an endotracheal tube positioned within the patient;
   (c) calculating the oscillatory pressure ratio from the peak-to-peak oscillatory pressures in the proximal and distal ends of the endotracheal tube;
   (d) decreasing the mean airway pressure provided to the patient;
   (e) recalculating the oscillatory pressure ratio at the decreased mean airway pressure;
   (f) repeating steps (d) and (e) until the oscillatory pressure ratio increases.

15. The method according to claim 14, further comprising the step of altering the mean airway pressure until the oscillatory pressure ratio is at or near its minimum value.

16. The method according to claim 14, wherein the measuring of the peak-to-peak oscillatory pressures in the proximal and distal ends is done on a periodic basis.

17. The method according to claim 14, wherein the measuring of the peak-to-peak oscillatory pressures in the proximal and distal ends is done on a continuous basis.

18. The method according to claim 14, further comprising the step of displaying the oscillatory pressure ratio on a display device.

19. The method according to claim 14, further comprising the step of altering the oscillatory frequency after the oscillatory pressure ratio is at or near its minimum value.

20. A device for determining the optimum mean airway pressure for a patient on high frequency oscillatory ventilation, the patient being incubated with an endotracheal tube, the device comprising:
   a first pressure sensor at a proximal end of the endotracheal tube;
   a second pressure sensor at the distal end of the endotracheal tube;
   means for calculating the oscillatory pressure ratio based on measurements obtained from the first and second pressure sensors;
   a mean airway pressure controller for altering the mean airway pressure delivered to the patient; and
   a display for displaying the oscillatory pressure ratio.

21. A device according to claim 20, the means for calculating the oscillatory pressure ratio comprising a microprocessor.

22. A device according to claim 21, wherein the first and second pressure sensors are pressure transducers.

23. A device according to claim 22, wherein the first and second pressure sensors are coupled to an amplifier.

24. A device according to claim 23, wherein the output of the amplifier is coupled to a peak/valley detector which outputs to the microprocessor.

25. A device for determining the optimum mean airway pressure for a patient on high frequency oscillatory ventilation, the patient being intubated with an endotracheal tube, the device comprising:
- a pressure sensor positioned at a distal end of a pressure tip transducer, the pressure tip transducer being axially moveable within the endotracheal tube to proximal and distal positions;
- means for calculating the oscillatory pressure ratio based on measurements obtained from the pressure sensor;
- a mean airway pressure controller for altering the mean airway pressure delivered to the patient; and
- a display for displaying the oscillatory pressure ratio.

26. A device for setting the desired mean airway pressure for a patient on high frequency oscillatory ventilation, the patient being intubated with an endotracheal tube, the device comprising:
- at least one pressure sensor for measuring peak-to-peak oscillatory pressures at a proximal end and a distal end of the endotracheal tube;
- a microprocessor operatively coupled to the at least one pressure sensor, the microprocessor calculating an oscillatory pressure ratio based on the measured peak-to-peak oscillatory pressures;
- a mean airway pressure controller for altering the mean airway pressure delivered to the patient, the mean airway pressure controller being operatively coupled to the microprocessor; and
- wherein the microprocessor automatically adjusts the mean airway pressure delivered to the patient such that the oscillatory pressure ratio is at or near its minimum value.

27. A device according to claim 26, further comprising a display for display the oscillatory pressure ratio.

* * * * *